(12) United States Patent
Mittereder et al.

(10) Patent No.: US 11,346,767 B2
(45) Date of Patent: May 31, 2022

(54) DETECTOR CELL FOR A PHOTOACOUSTIC GAS SENSOR AND PHOTOACOUSTIC GAS SENSOR

(71) Applicant: Infineon Technologies AG, Neubiberg (DE)

(72) Inventors: Tobias Mittereder, Munich (DE); Christoph Glacer, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 58 days.

(21) Appl. No.: 16/935,726

(22) Filed: Jul. 22, 2020

(65) Prior Publication Data
US 2021/0055207 A1 Feb. 25, 2021

(30) Foreign Application Priority Data
Aug. 22, 2019 (EP) .................................. 19193158

(51) Int. Cl.
*G01N 21/17* (2006.01)
*G01N 33/00* (2006.01)

(52) U.S. Cl.
CPC ........ *G01N 21/1702* (2013.01); *G01N 33/004* (2013.01); *G01N 2021/1704* (2013.01); *G01N 2021/1708* (2013.01); *G01N 2223/508* (2013.01)

(58) Field of Classification Search
CPC ............ G01N 21/1702; G01N 33/004; G01N 2223/508; G01N 2021/1704; G01N 2021/1708
See application file for complete search history.

(56) References Cited

U.S. PATENT DOCUMENTS

| | | |
|---|---|---|
| 2015/0101395 A1 | 4/2015 | Dehe et al. |
| 2016/0282259 A1 | 9/2016 | Kolb et al. |
| 2016/0313288 A1 | 10/2016 | Theuss et al. |
| 2019/0208330 A1 | 7/2019 | Bretthauer et al. |
| 2019/0257796 A1* | 8/2019 | Duraffourg ........ G01N 29/2425 |

FOREIGN PATENT DOCUMENTS

| | | |
|---|---|---|
| GB | 2358245 A | 7/2001 |
| WO | 2017207399 A1 | 12/2017 |

* cited by examiner

*Primary Examiner* — Benjamin R Schmitt
(74) *Attorney, Agent, or Firm* — Slater Matsil, LLP

(57) ABSTRACT

A detector cell for a photoacoustic gas sensor comprises a first layer structure, a second layer structure arranged at the first layer structure and comprising a membrane structure, and a third layer structure arranged at the second layer structure. The first layer structure and the third layer structure hermetically enclose a cavity, wherein the membrane structure is arranged in the cavity.

26 Claims, 19 Drawing Sheets

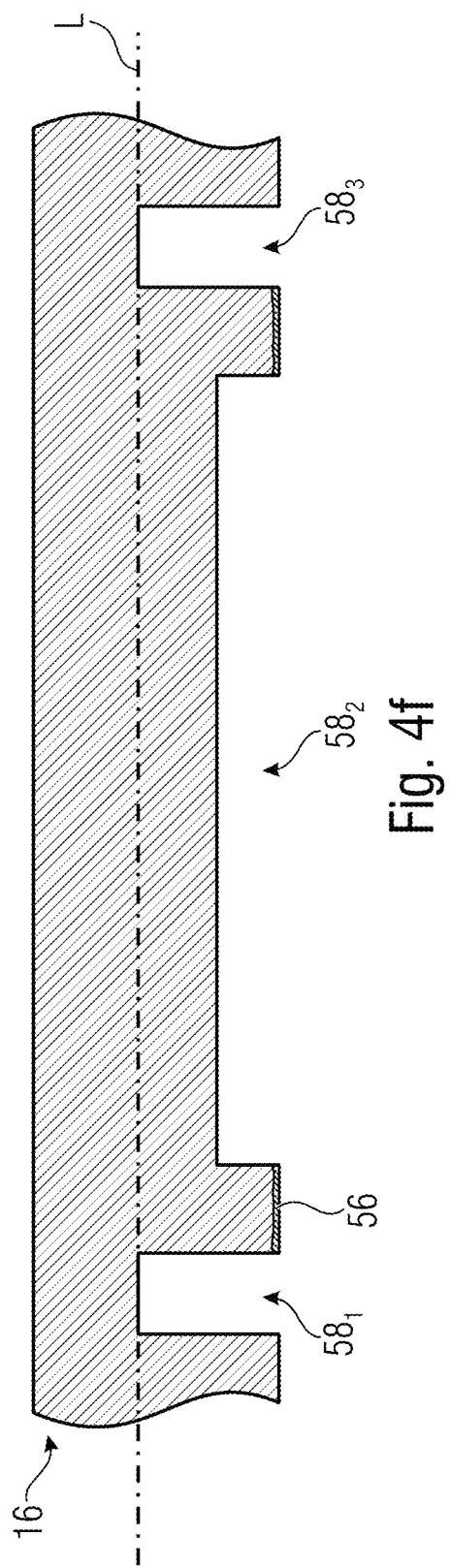

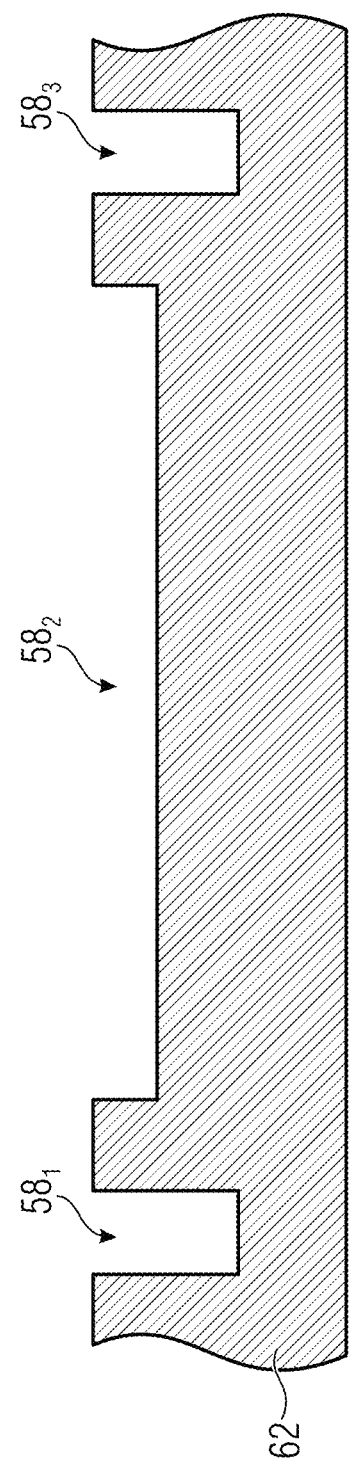

DETECTOR CELL FOR A PHOTOACOUSTIC GAS SENSOR AND PHOTOACOUSTIC GAS SENSOR

This application claims the benefit of European Patent Application No. 19193158, filed on Aug. 22, 2019, which application is hereby incorporated herein by reference.

TECHNICAL FIELD

The present disclosure is related to a detector cell for a photoacoustic gas sensor, to photoacoustic gas sensors and to methods for fabricating a detector cell and a photoacoustic gas sensor. The present disclosure further relates to a wafer level bonded photoacoustic detector cell.

BACKGROUND

Photoacoustic gas sensors may be used to measure environmental conditions, for example, portions of a fluid, in particular a gas.

There is a request for a detector cell and for photoacoustic gas sensors having a high durability and being robust over a lifetime. There is further a request for methods for fabricating a detector cell and photoacoustic gas sensors.

SUMMARY

Embodiments provide for a detector cell for a photoacoustic gas sensor. The detector cell comprises a first layer structure, a second layer structure arranged at the first layer structure and comprising a membrane structure and comprises a third layer structure arranged at the second layer structure. The first layer structure and the third layer structure hermetically enclose a cavity, wherein the membrane structure is arranged in the cavity. By enclosing a cavity between the first and the third layer structure, the sealing to hermetically enclose the cavity may have a high durability and a high robustness.

An embodiment provides for a photoacoustic gas sensor comprising such a detector cell and comprising an electromagnetic source configured for emitting an electromagnetic radiation so as to excite a movement of the membrane structure based on an asymmetric energy absorption of the electromagnetic radiation in different sub-cavities of the cavity, the different sub-cavities arranged on different sides of the membrane structure.

Embodiments provide for a chip-scaled packaged photoacoustic gas sensors comprising a detector cell having a membrane structure inside a detector cell cavity, having a first sub-cavity of the cavity at a first side of the membrane structure and having a second sub-cavity of the cavity at a second, opposing side of the membrane structure. The chip-scaled packaged photoacoustic gas sensor comprises an electromagnetic source configured for emitting an electromagnetic radiation so as to excite a movement of the membrane structure based on a asymmetric energy absorption of the electromagnetic radiation in the first sub-cavity and the second sub-cavity.

An embodiment provides for a method for manufacturing a detector cell. The method comprises providing a first layer structure, attaching a second layer structure having a membrane structure at the first layer structure and attaching a third layer structure at the second layer structure. The method is carried out such that the first layer structure and the third layer structure hermetically enclose a cavity and such that the membrane structure is arranged in the cavity.

An embodiment provides for a method for manufacturing a photoacoustic gas sensor. The method comprises providing a detector cell having a membrane structure inside a detector cell cavity, a first sub-cavity of the cavity at a first side of the membrane structure, and a second sub-cavity of the cavity at a second, opposing side of the membrane structure. The method comprises arranging an electromagnetic source configured for emitting an electromagnetic radiation so as to excite a movement of the membrane structure based on an asymmetric energy absorption of the electromagnetic radiation in the first sub-cavity and the second sub-cavity.

BRIEF DESCRIPTION OF THE DRAWINGS

Further embodiments are described in the dependent claims.

Embodiments will be described in the following while making reference to the accompanying drawings in which:

FIG. 2b is a schematic perspective exploded diagram of the detector cell of FIG. 2a;

FIGS. 4a-4k are example processing steps for manufacturing a detector cell according to an embodiment;

DETAILED DESCRIPTION OF ILLUSTRATIVE EMBODIMENTS

Figure 1:
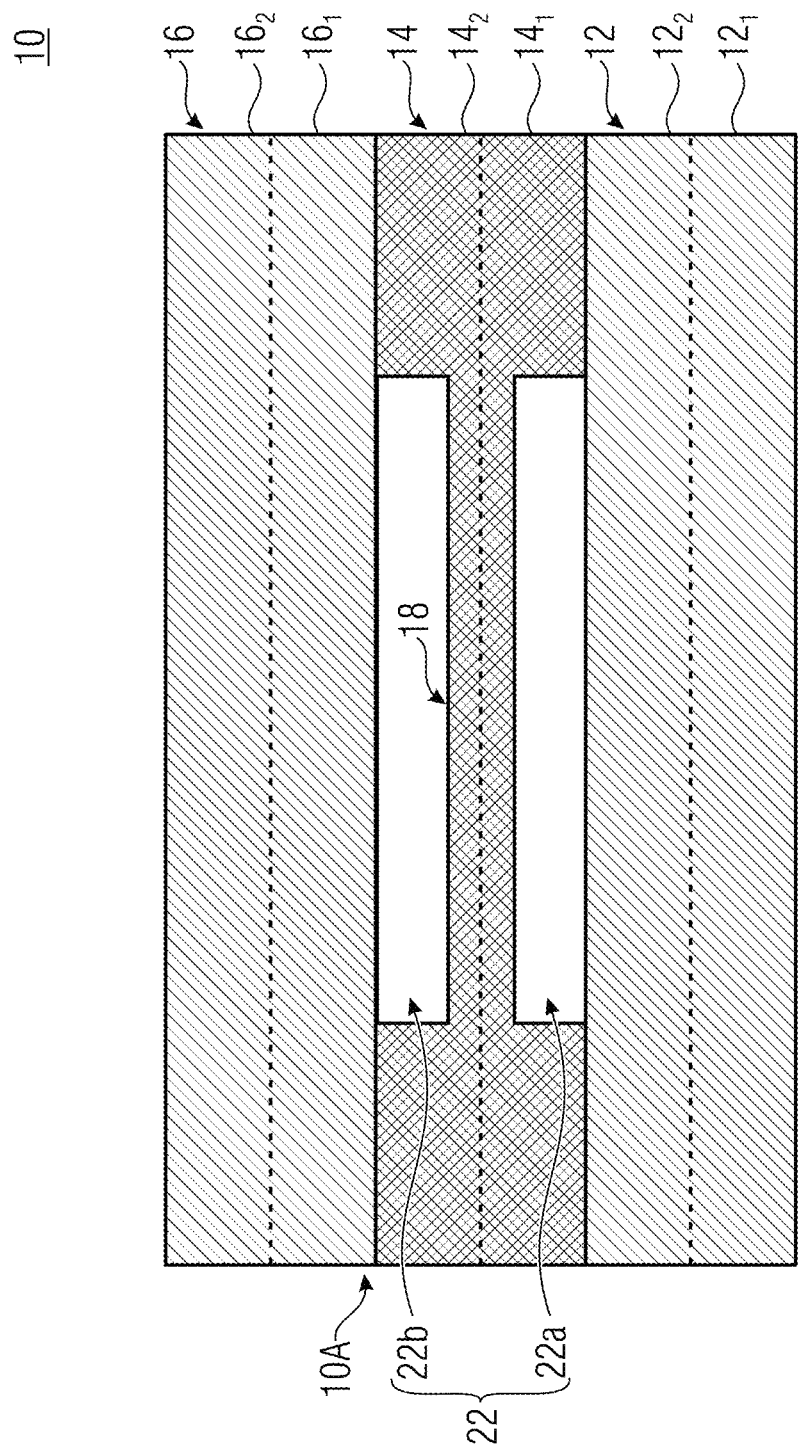
FIG. 1 is a schematic side view of a detector cell according to an embodiment.

Equal or equivalent elements or elements with equal or equivalent functionality are denoted in the following description by equal or equivalent reference numerals even if occurring in different figures.

In the following description, a plurality of details is set forth to provide a more thorough explanation of embodiments of the present invention. However, it will be apparent to those skilled in the art that embodiments of the present invention may be practiced without these specific details. In other instances, well known structures and devices are shown in block diagram form rather than in detail in order to avoid obscuring embodiments of the present invention. In addition, features of the different embodiments described hereinafter may be combined with each other, unless specifically noted otherwise.

Embodiments described herein relate to photoacoustic gas sensors and to detector cells that may be used in such photoacoustic gas sensors. Such a photoacoustic gas sensor may comprise a detector cell in which a target gas, i.e., molecules or same or different type, are enclosed. That is, a single gas or a combination of gases or fluids may be enclosed. Such a detector cell may be arranged in a housing of a photoacoustic gas sensor, the photoacoustic gas sensor comprising a source of electromagnetic radiation. Further details in view of a working principle of a photoacoustic gas sensor are described in connection with disclosed embodiments.

Embodiments are related to a detector cell being a microelectromechanical structure (MEMS). A MEMS structure may comprise one or more semiconductor materials, for example, an at least partially doped or undoped semiconductor material such as silicon, gallium, arsenide or the like. Materials derived therefrom such as a silicon nitride (SiN, $Si_3N_4$, respectively), silicon oxide ($SiO_2$) or the like may be arranged alternatively or in addition. Alternatively or in addition, other materials such as a metal material, e.g., copper, gold, silver, platinum or the like, may be part of a MEMS structure.

Embodiments described herein may relate to a membrane structure. Such a membrane structure may be understood as a beam-like structure (having a longitudinal extension being larger than a lateral extension perpendicular hereto), but may also be a planar or two-dimensional structure in which lateral extensions perpendicular to each other are equal with respect to each other within a tolerance range. An example for such a structure may be a circular structure, e.g., a round or circular membrane, or a quadratic membrane structure. Such a membrane structure may be formed, for example, similar to a membrane structure being used in MEMS microphones or MEMS loudspeakers.

FIG. 1 is a schematic side view of a detector cell 10 according to an embodiment. The detector cell 10 may be usable or integratable into a photoacoustic gas sensor. That is, the detector cell 10 may form a component of a photoacoustic gas sensor but may be implemented separately or individually.

The detector cell 10 may comprise a first layer structure 12, a second layer structure 14 and a third layer structure 16 arranged as a stack of layer structures. That is, the layer structure 14 may be arranged at the layer structure 12. The layer structure 16 may be arranged at the layer structure 14. The layer structure 12 may comprise one or more layers. For example, the layer structure 12 may comprise two layers $12_1$ and $12_2$, wherein the layers $12_1$ and $12_2$ may comprise same or different materials.

Alternatively or in addition, the layer structure 14 may comprise one or more layers. For example, the layer structure 14 may comprise layers 141 and 142 having same or different materials. Alternatively or in addition, the layer structure 16 may comprise one or more layers. For example, the layer structure 16 may comprise layers $16_1$ and $16_2$ having same or different materials.

A number of layers of the layer structure 12, 14 and/or 16 may be implemented individually and equal or different with regard to a number of layers of other layer structures. A number of layers of each layer structure 12, 14 and 16 may be, for example, one, two, three, four, five or higher, e.g., seven or ten.

The layer structure 14 may comprise a membrane structure 18. The membrane structure 18 may comprise one or more layers, for example, a semiconductor layer a semiconductor layer and a conductive layer, e.g., a doped semiconductor material or a metal material, covering at least parts of one or two sides of the membrane structure 18. The membrane structure 18 may be arranged such that sub-cavities 22a and 22b of a cavity 22 are arranged on different sides of the membrane structure 18. For example, a recess may be implemented in the layer structure 12 and/or the layer structure 14 so as to form sub-cavity 22a. Alternatively or in addition, a recess may be formed in the layer structure 14 and/or the layer structure 16 so as to form sub-cavity 22b. That is, embodiments relate to a structure having only one of sub-cavities 22a and 22b, wherein further embodiments relate to structures having sub-cavity 22a and sub-cavity 22b. Sub-cavity 22a may be fluidically connected to sub-cavity 22b or may be sealed from sub-cavity 22b.

Layer structure 12 and layer structure 16 thus hermetically enclose cavity 22. The membrane structure 18 is arranged in the cavity. To hermetically enclose the cavity 22, the layer structure 12 and the layer structure 18 may be connected to each other so as to form a hermetically tight mechanical connection. Further, layer structures 14 and 16 may be connected to each other so as to form a hermetically tight mechanical connection with respect to each other. This is different when compared to a cavity in which a structure is arranged which itself hosts a cavity in which a membrane is arranged. According to embodiments, it is enabled to generate the cavity 22 directly via mechanically connecting layer structures to each other. The layer structure 14 may form at least a part of a sidewall 10A of the detector cell 10.

The cavity 22 may comprise or host a fluid, for example, a gas being a target gas for a later photoacoustic gas sensor.

Figure 2A:
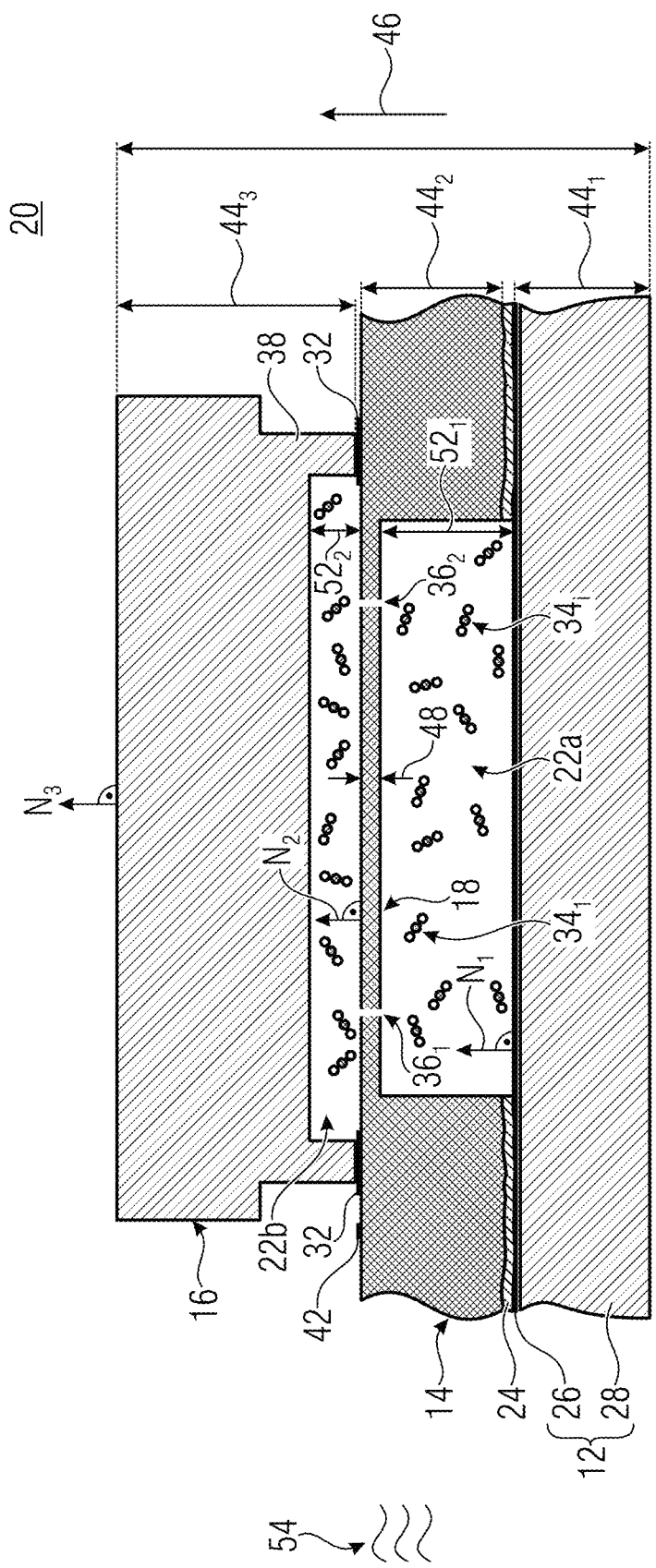
FIG. 2a is a schematic side view of a further detector cell according to an embodiment.

FIG. 2a shows a schematic side view of a detector cell 20 according to an embodiment. The layer structures 12 and 16 may comprise, for example, semiconductor materials, conductive materials and/or insulating materials. For example, the layer structure 12 may comprise a glass material or a ceramic material as an insulating material. As a semiconductor material, for example, a silicon material or a gallium-arsenide material may be used. As a conductive material, for example, a metal material such as gold, silver, aluminum, copper or the like, including allays, may be used. Alternatively or in addition, a doped semiconductor material may be used. For example, the layer structure 12 may be obtained from a glass wafer or a silicon wafer. In connection with the described embodiments, the layer structure 12 may be referred to as a bottom sealing wafer. The layer structure 16 may, in contrast, be referred to as a top sealing cap wafer and may comprise, for example, a semiconductor material or an insulating material. A semiconductor material such as silicon may allow for generating or obtaining sub-cavity 22b as a recess in the layer structure 16, whilst a glass material does not exclude such a configuration but may provide for an increased hardness of the material. Sub-cavity 22a may be formed at least partially as a recess in the layer structure 14.

The layer structure 14 may comprise a structure that corresponds, essentially, to a Si-microphone structure. For example, the membrane structure 18 may be a multi-layer structure.

Layer structures 12 and 14 may be bonded to each other, for example, during a wafer bonding process. For example, between the layer structures 12 and 14, a boundary layer or an interface 24 may be arranged. The interface 24 may be a result of the wafer bonding process. For example, a material arranged at the layer structure 12 and a material of the layer structure 14 may each form a part of the interface 24.

For example, the layer structure 12 may comprise a coating layer 26 and a substrate layer 28. The substrate layer 28 may comprise, for example, a conductive, insulating or semiconductor material such as a silicon material. At least in a region of a later mechanical connection to the layer structure 14, the coating layer 26 may be arranged, for example, comprising a metal material, e.g., a gold material, wherein, alternatively, other materials such as aluminum or other reflective metallic or non-metallic materials or structures. For example, gold (Au) and aluminum (Al) may be used for implementing a eutectic bond. Such a material may, at a same time, provide for reflective properties. This does not exclude to use different materials for bonding and for the reflective surface.

Further, embodiments are not limited hereto. For example, a glass frit may be used for bonding. Any reflective structure or material may be used as coating layer 26. For example, Au may be inert and optically stable. Alternatively or in addition, a Bragg mirror structure may be used. For example, such a structure may be obtained from $Si/SiO_2$ material for the present embodiments. That is, the coating layer 26 may form a surface being reflective for electromagnetic radiation and may comprise at least one of a reflective material and a reflective structure.

During the wafer bonding process, the material of the coating layer 26 and the material of the layer structure 14 may form the interface 24, thereby providing a tight mechanical connection and thus a part of the hermetic sealing.

The coating layer 26 may, optionally, be arranged in a region of the cavity, the sub-cavity 22a and/or the sub-cavity 22b. This may allow for a reflective surface, e.g., to reflect thermal radiation or other electromagnetic radiation.

The coating layer 26 may provide for a surface reflective for electromagnetic radiation. The coating layer 26 may be arranged at surface of the layer structure 12 so as to face the membrane structure 18. Alternatively or in addition, the coating layer 26 may be arranged at the layer structure 16 so as to face the membrane structure 18. The coating layer 26 may allow to prevent an entry of electromagnetic radiation into the shielded sub-cavity, e.g., from a bottom side of FIG. 2a. Alternatively or in addition, the coating layer 26 may allow reflection of electromagnetic radiation 54 that has already entered the cavity so as to prevent an escape of the radiation.

In a same or a different manner, between the layer structures 14 and 16 a coating structure or coating layer 32 may be arranged, for example, comprising a gold material, an aluminum material or the like For example, a combination of materials may be arranged, e.g., gold/tin (AuSn). By way of wafer level bonding, layer structures 14 and 16 may be combined or connected to each other as described for the layer structures 12 and 14.

Embodiments relate to host a target medium such as a fluid, e.g., a gas as illustrated by example molecules $34_1$ to $34_i$ in the cavity. A target medium may be, for example, $CO_2$, $CO$, $NO_2$ or any other suitable fluid such as $CH_4$ (Methane) and $SO_2$. For example, the membrane structure 18 may comprise connections between sub-cavity 22a and sub-cavity 22b, for example, implemented by ventilation holes $36_1$ and $36_2$, wherein a number of ventilation holes may be different, for example, 0, 1, 3 or more, 5 or more, 10 or more, 20 or more, or even higher numbers. This may allow obtaining a connection between the layer structures 12 and 14 and/or between the layer structures 14 and 16 differently. For example, the layer structures 12 and 14 and/or the layer structures 14 and 16 may be formed as a common layer structure out of which a respective sub-cavity 22a or 22b is formed, for example, using an etching process. This may allow avoiding a wafer level bonding as a target gas may reach the respective sub-cavity 22a or 22b by use of the ventilation.

Nevertheless, a wafer level bonding process may allow for a precise and hermetically tight connection between layer structures. The coating layer 32 may be used as, for example, a seal ring and may have, for example, a ring-like structure corresponding to a structure of a protruding 38 of the layer structure 16. Optionally, conductive structures 42, e.g., bond pads or the like for connecting one or more conductive layers, e.g., of the membrane structure 18 and/or a backplate structure, may be arranged. The conductive structure 42 may be formed, at least in parts, by same materials when compared to the coating layer 32 which allows for simple processes. For example, the coating structure 32 may easily be formed in addition to the conductive structures 42 without severely changing manufacturing processes.

Using wafer level bonding processes may allow to fabricate or generate or manufacture a plurality of detector cells in parallel and to separate them afterwards easily, for example, using a dicing process.

The layer structures 12, 14 and/or 16 may have some or different extensions $44_1$, $44_2$, $44_3$ respectively along a thickness direction 46. The thickness direction 46 may be parallel to a surface normal $N_1$ of layer structure 12, to a surface normal $N_2$ of layer structure 14 and/or to a surface normal $N_3$ of layer structure 16. The surface normals $N_1$, $N_2$ and/or $N_3$ may be perpendicular to N-plane directions along which a wafer that forms or has previously formed one or more layers of layer structures 12, 14, 16, respectively mainly or basically and extends. For example, layer structure 12 may form a substrate. For example, a maximum extension $44_1$ or layer structure 12 may be arbitrary, wherein a thin layer structure 12 may be desirable whilst maintaining a certain stability. Within these boundaries, example extensions $44_1$ may be at least 20 μM and at most 1 mm, at least 50 μm and at most 800 μm or at least 70 μm and at most 500 μm. The extension $44_2$ may have any value, for example, at least 100 μm and at most 1 mm, at least 250 μm and at most 500 μm or at least 250 μm and at most 400 μm. The extension $44_2$ may be implemented such that it is a summarized value of a thickness 48 of membrane structure 18 along the thickness direction 46 and of a thickness or height $52_1$ of sub-cavity 22a. For example, thickness 48 may be in a range of at least 1 μm and at most 10 μm, of at least 2 μm at most 7 μm or at least 3 μm and at most 5 μm, e.g., 4 μm. For example, the height $52_1$ may be in a range of at least 100 μm and at most 990 μm, of at least 150 μm and at most 700 μm or at least 200 μm and at most 500 μm, e.g., in a range between 246 μm and 396 μm. Alternatively, the height $52_1$ may be a result of using or further processing a starting structure of layer structure 14 that has the extension $44_2$. After forming the membrane structure 18 by generating a recess, the sub-cavity 22a, the height $52_1$ maybe a result of the desired thickness 48. Other values and sequences may be implemented. Alternatively or in addition, the extension $44_3$ may have any suitable value, for example, at least 50 μm and at most 1 mm, at least 100 μm and at most 500 μm or at least 150 μm and at most 300 μm. The extension $44_3$ exceeds a thickness or height $52_2$ of sub-cavity 22b which may be, for example, at least 1 μm and at most 500 μm, at least 2 μm and at most 400 or at least 5 μm and at most 300 μm, e.g., in a range of at least 10 μm and at most 200 μm. The extension $44_3$ may allow for a robust enclosure of sub-cavity 22b, i.e., it may comprise a larger extension $44_3$ when compared to the height $52_2$.

Alternatively or in addition, a combination of gases may be arranged. The molecules $34_1, \ldots, 34_i$ shown relate, by non-limiting example only, to $CO_2$.

The cavity 22, sub-cavity 22a and/or 22b respectively may be acoustically isolated. That is, the membrane 18 is vibratable with respect to acoustic sound at an exterior of the respective sub-cavity 22a and/or 22b only to a negligible effect or is insensitive to acoustic sound.

The layer structure 12, the layer structure 14 and/or the layer structure 16 may at least in parts be transparent for an electromagnetic radiation 54. This may allow the electromagnetic radiation 54 to travel into the cavity 22, sub-cavity 22a and/or 22b respectively, so as to excite membrane 18 to vibrate. For example, the layer structure 14 is transparent for the electromagnetic radiation 54. The layer structures 12, 14, and/or 16 may be transparent for a wavelength of an emitter to be combined with the detector cell. For example, the layer structures 12, 14 and/or 16 may be transparent for an infrared spectrum, in particular, a mid-wavelength infrared spectrum. Whilst the infrared spectrum may comprise wavelengths of at least 760 nm to at most 1 mm, the mid-wavelength infrared spectrum may comprise wavelengths of at least 1 μm and at most 100 μm, of at least 2 μm and at most 70 μm or at least 3 μm and at most 50 μm.

The detector cell 20 may be formed such that the detector cell 20 is asymmetric with regard to a sensitivity to the electromagnetic radiation in the sub-cavity 22a and in the sub-cavity 22b. Such an asymmetry may be understood as having different forces in view of magnitude, frequency or time offset with regard to a generation of the electromagnetic radiation 54 so as to prevent equal forces acting on the membrane structure 18 in both sub-cavity 22a and 22b which might cancel out the vibration of the membrane 18. By implementing the asymmetry, the electromagnetic radiation 54 may comprise a high sensitivity to the electromagnetic radiation 54. As will be described later in more detail, the asymmetry may be generated alternatively or in addition to having different heights $52_1$ and $52_2$ by other means. That is, an asymmetry may be obtained at least partially by implementing extensions $52_1$ and $52_2$ so as to be different, for example, 1:1.1, 1:1.2 or 1:1.5 or higher numbers.

Alternatively or in addition, the sub-cavities 22a and 22b may be shielded different, shielding one sub-cavity whilst not shielding the other or shielding to a different extent such that the electromagnetic radiation 54 penetrates or pierces the sub-cavities 22a and 22b differently. Alternatively or in addition, different pressures of the target gas 34 may be implemented, for example, in structures having sub-cavities being sealed from each other.

Alternatively or in addition, for obtaining the asymmetry, the sub-cavities 22a and 22b may be sealed from each other and may comprise different gases or gas concentrations. By using different gases, the detector cell may be implemented so as to be sensitive for two gases. For example, the absorption characteristic of both gases may be disjoined in the wavelength-range or frequency-range such that the excitation of the membrane structure 18 may clearly be distinguishable when evaluating the vibration of the membrane structure 18.

Figure 2B:
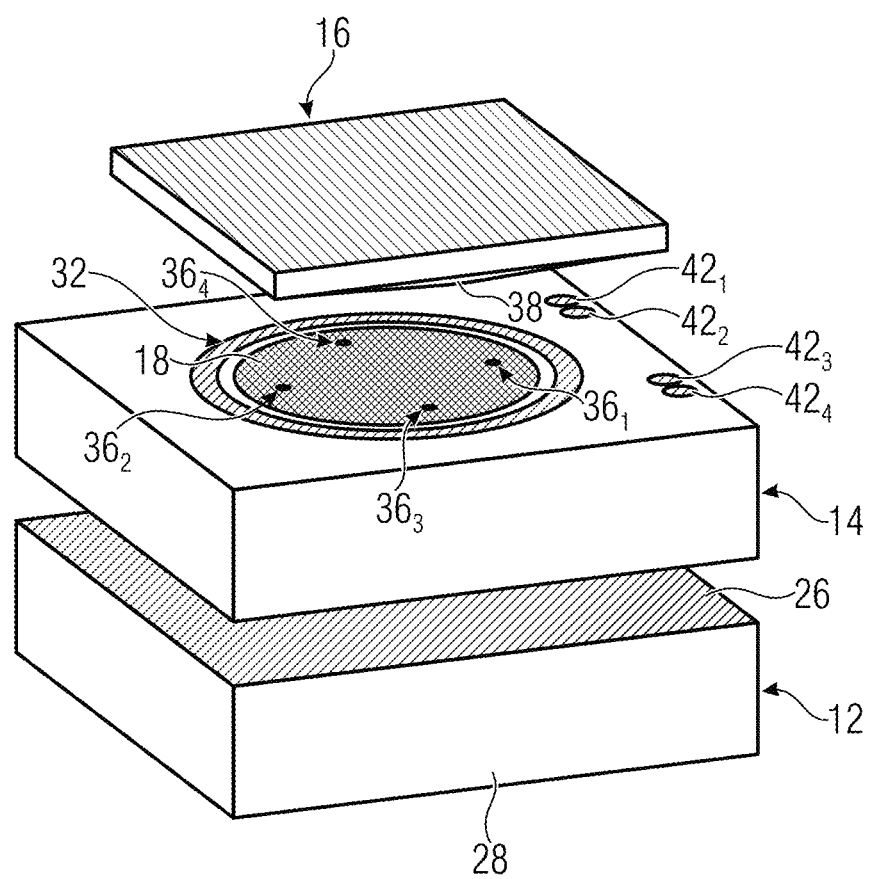

FIG. 2b shows a schematic perspective exploded diagram of the detector cell 20 to illustrate, for example, the circumferential course of the coating structure 32, i.e., the seal ring. The membrane structure 18 may be formed, for example, as a round or circular structure. Although four ventilation holes $36_1$ to $36_4$ are illustrated, a different number, e.g., 0 or more, 1 or more, 2 or more, 3 or more, 5 or more or a higher number may be implemented. That is, the membrane structure may comprise at least one ventilation hole.

Insert to bottom sealing wafer: Terms like bottom, top, left, right and the like are used to facilitate the understanding of the present disclosure. It is clear that based on a varying orientation of the structure the appropriate terms may vary without changing the scope of the embodiments.

In other words, the Si-microphone wafer with top sealing wafer and bottom sealing wafer is shown. A dedicated gas atmosphere such as any concentration of more than 0% and at most 100% of the target gas, e.g., $CO_2$ may be enclosed during a bonding step, for example a last bonding step. A concentration of 100% may provide for a high sensitivity wherein a lower concentration may allow for combination of gases and thus for multiple sensitivities. A pressure of the target gas, may be higher or lower when compared to an ambient pressure of the later device. For example, a pressure may be of at least 10 mbar and at most 5 bar or any other suitable value, e.g., to enhance or reduce the absorption of electromagnetic radiation.

The steps may be implemented so as to first provide for a backside sealing (Au/Si eutectic bond) and to then seal under a $CO_2$ atmosphere (AuSn soldering of cap structure to metal ring on Si-MEMS topside). Those steps may be performed in different order. The bond pads of the microphone may remain accessible after the WLB processes. The whole step of silicon wafers may be transparent for the mid-wavelength infrared spectrum, which may be used for optical excitation in gas sensing.

Figure 3:
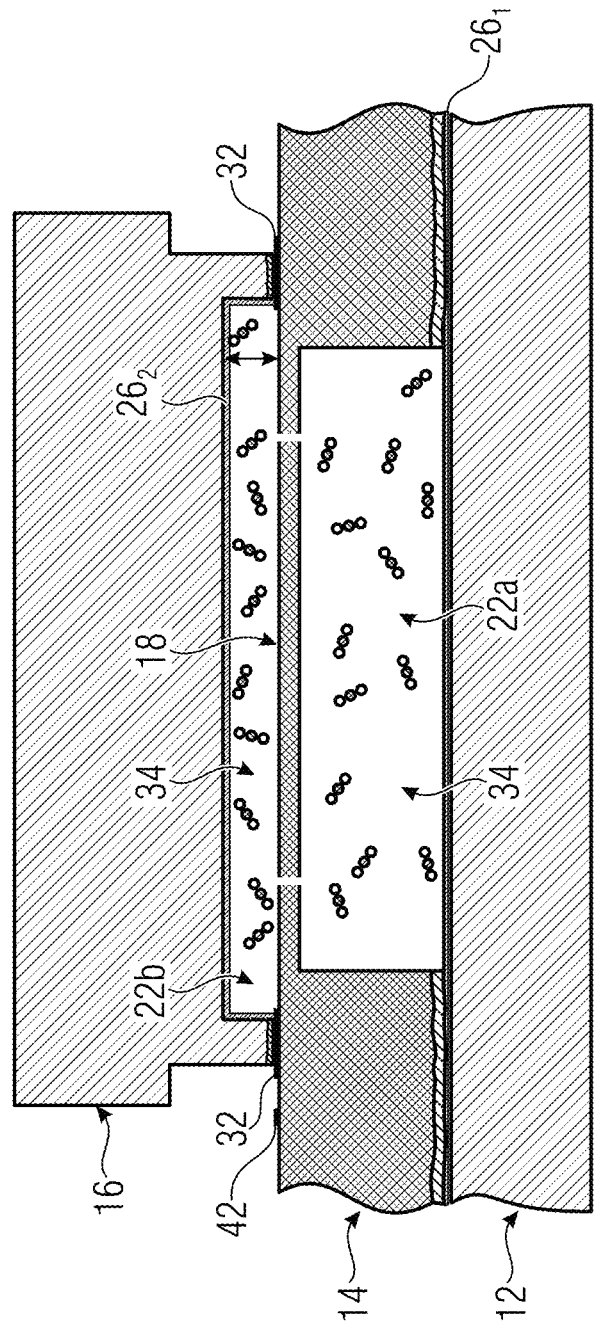
FIG. 3 is a schematic side view of a detector cell according to an embodiment having a coating layer.

FIG. 3 shows a schematic side view of a detector cell 30 according to an embodiment. The detector cell 30 may be formed similar to the detector cell 20. When compared to the detector cell 20, beside a coating layer $26_1$ which may be the coating layer 26 of detector cell 20, another coating layer $26_2$ may be arranged at the layer structure 16 or as a part thereof, for example, so as to face the membrane structure 18. Although the coating layer $26_1$ and the coating layer $26_2$ both are optional, the configuration of detector cell 20 and of detector cell 30 allows that a part of the cavity is sealed by a reflective coating from light or electromagnetic radiation adapted to excite the target medium 34 in the cavity.

The membrane structure 18 described in connection with detector cell 10, 20 and/or 30 may be evaluated for a vibration thereof. The detector cell 10, 20 and/or 30 may comprise a circuitry being configured for evaluating the vibration. Alternatively or in addition, the detector cell 10, 20 and/or 30 may be connectable to a suited circuitry, for example, using conductive structures 42. The membrane structure 18 may be arranged, for example, in a single-backplate configuration or a dual-backplate configuration. A single-backplate configuration may refer to a configuration according to which a vibration of the membrane having a conductive surface is evaluated with regard to one counter electrode arranged adjacent to the membrane. In a dual-backplate configuration, for example, the vibratable membrane may be sandwiched between two counter-electrodes. That is, the layer structure 14 may comprise a single backplate configuration or a dual-backplate configuration for the membrane structure 18. Alternatively or in addition, the detector cell 10, 20 and/or 30 may comprise a piezoelectric or a piezo-resistive element so as to determine a deformation or vibration of the membrane structure 18.

Whilst making reference to FIGS. 4a to 4k example processing steps for manufacturing a detector cell 10, 20 and/or 30 are described in the following. It is noted that the figures neither limit such a manufacturing process to a specific sequence or order of steps nor are all of those steps necessary to manufacture for a detector cell in accordance of embodiments nor are further steps precluded.

Figure 4A:
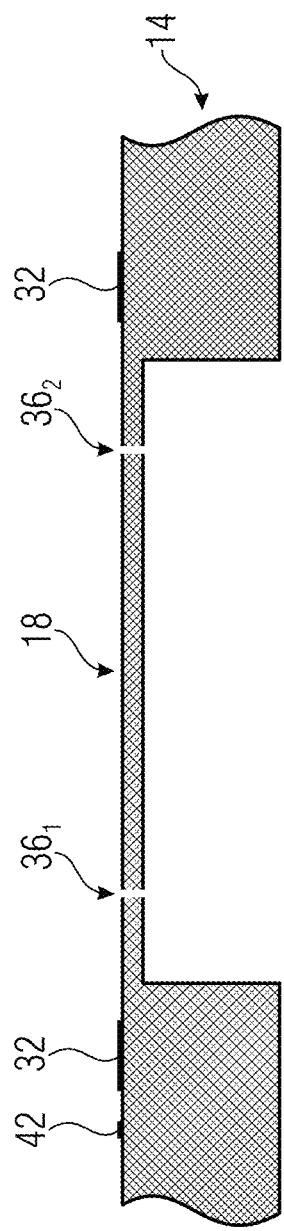

FIG. 4a shows a schematic side view of the layer structure 14 having the microphone structure 18, the seal ring 32 and conductive structure 42. The conductive structure 42 may be, for example, a metallization using a metal material such as gold, silver, aluminum, copper or the like. The membrane structure 18 may be a single backplate structure or a dual backplate structure. In the figures of the present disclosure, the membrane structure and counter electrodes are displayed as a single block so as to facilitate the understanding of embodiments. The layer structure 14 may be similar to a silicon based microphone structure. A native insulating layer, for example, $SiO_2$ on a substrate backside may be removed, for example, using a HF (hydrogen fluoride) dip.

Figure 4B:
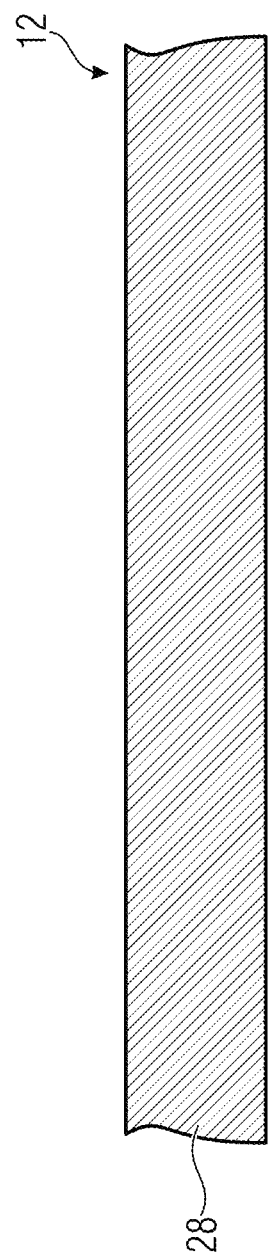

FIG. 4b shows a schematic side view of a configuration of the layer structure 12, for example, comprising the substrate layer 28 at the present stage. The substrate layer 28 may be, for example, at least a part of a silicon wafer but may also comprise other materials. By way of example, the substrate layer 12 may be a wafer to be diced or separated later.

Figure 4C:
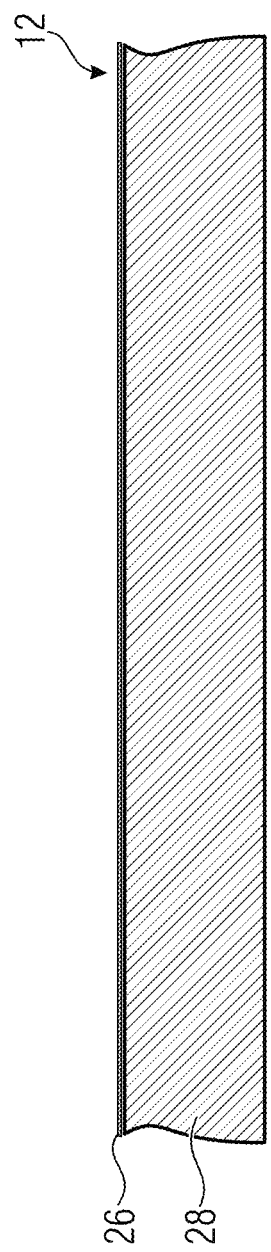

FIG. 4c shows a schematic side view of the layer structure 12. When compared to FIG. 4b, the coating layer 26 has been arranged, for example, over the complete wafer or at least large structures thereof. The deposition of the coating layer 26 may comprise a deposition of a metal material such as gold or the like on the silicon wafer. The deposition of the coating layer 26 may include a deposition of an adhesion layer, for example, tin (Ti). The coating layer 26 may serve for multiple purposes. For example, it may serve for forming an alloy with the layer structure 14 when performing a wafer level bonding (WLB). Further, it may serve as a reflection plane for optical radiation, e.g., electromagnetic radiation 54.

Figure 4D:
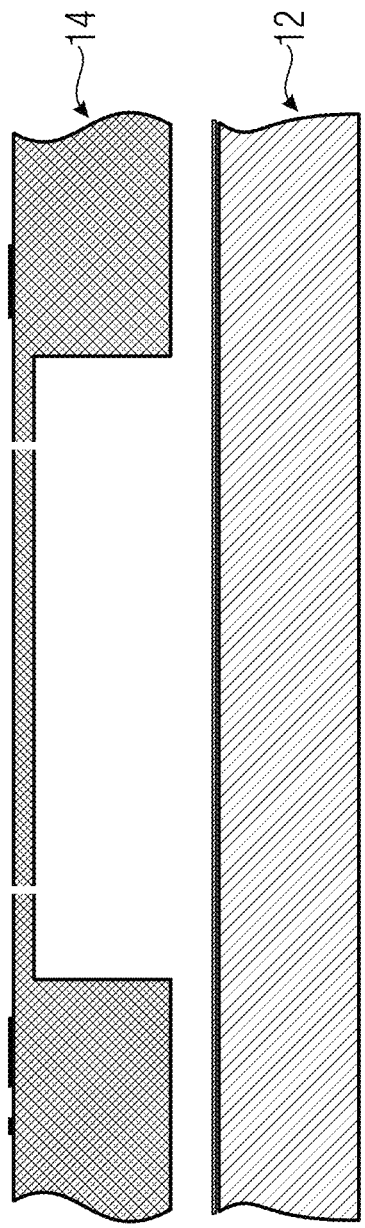
Figure 4E:
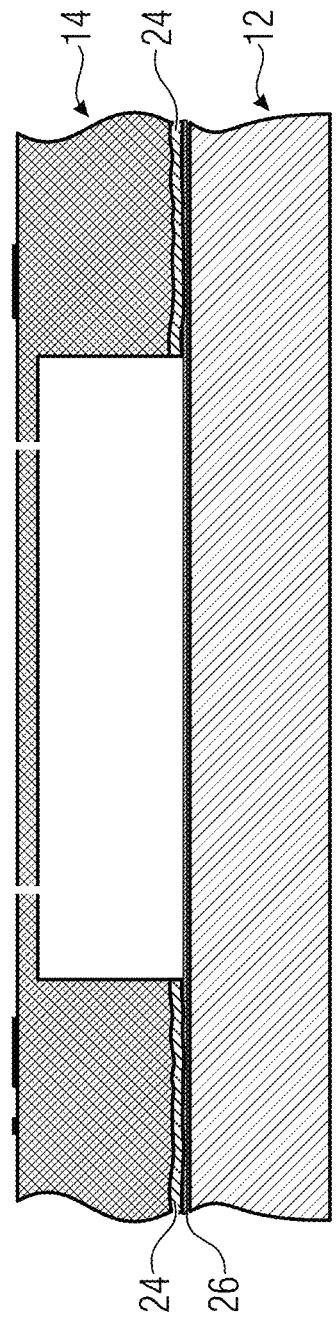
Figure 4G:
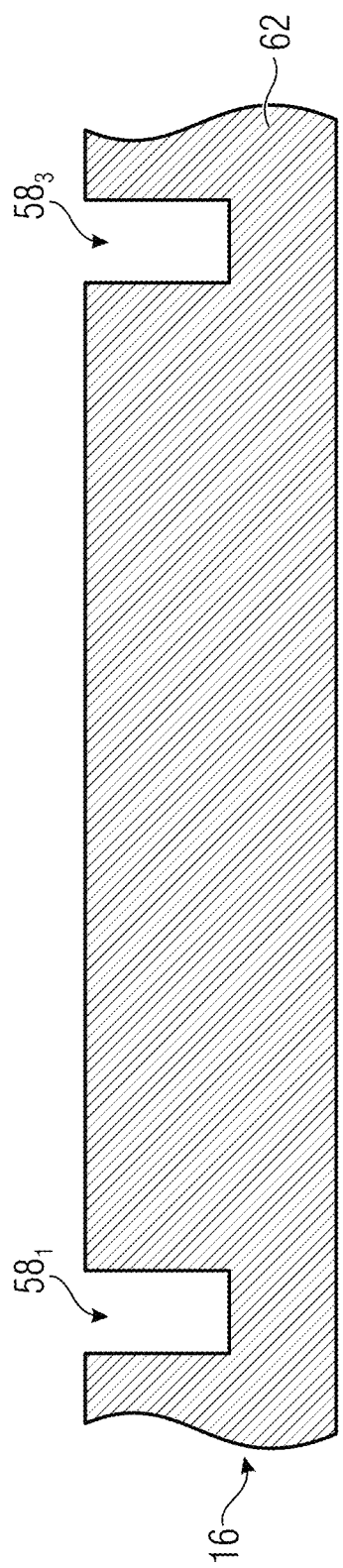

FIG. 4d shows a schematic side view of a configuration of layer structures 12 of FIG. 4c and of layer structure 14 of FIG. 4a prior to a step of combining both layer structures whilst FIG. 4e shows a schematic side view of layer structures 12 and 14 after the wafer level bonding. Based on the wafer level bonding, the interface 24 may be obtained allowing for a tight connection of layer structures 12 and 14. The interface 24 may comprise the alloy comprising material of the coating layer 26 and of the semiconductor material of layer structure 14, e.g., silicon material. The described eutectic Au/Si bond may be performed, for example, under a vacuum atmosphere or any other suitable atmosphere as the target gas may be included later when the membrane structure 18 comprises ventilation holes. Alternatively, a sealed sub-cavity may be bonded under the target atmosphere.

FIG. 4f shows a schematic side view of layer structure 16, the layer structure 16 may comprise a topographic structure. In parts thereof, an interface forming material 56, e.g., a gold material, an aluminum material, a tin material or a silver material or the like, including materials forming an alloy, e.g., gold/tin may be arranged as described for the conductive layer 26. Recesses $58_1$, $58_2$, and/or $58_3$ may be arranged. Recess $58_2$ may later provide at least partially for the sub-cavity 22b whilst recesses $58_1$ and $58_3$ may allow for facilitating a later dicing. For example, material may be removed, e.g., based on etching or grinding, until a level indicated by a line L is reached. The recesses $58_1$, $58_2$ and/or $58_3$ may be optional. For example, the sub-cavity 22b may also be formed as a recess in the layer structure 14, e.g., when arranging the membrane structure 18 in a center of the layer structure 14 with regard to the extension $44_2$ illustrated in FIG. 2a.

In other words, a Si-cap may be built with a gold-Sn solder 56 at contact position. By having two or more cavities, the singulation of the final dies may be done by grinding. This may allow for preventing cracks in the structure.

For obtaining a structure illustrated in FIG. 4f, a silicon wafer may be used into which the recesses $58_1$ and $58_3$ may be structured, for example, using an action process. The recesses $58_1$ and $58_3$ may be a same recess, for example, having a rectangular, elliptic or circular course. That is, a structuring of a first cavity $58_1$, $58_3$ may be performed into a silicon wafer 62.

Prior or after generating the recess $58_1$ and/or $58_3$, the recess $58_2$ may be generated, for example, using an etching process. Etching may be performed as wet etching or dry etching or other concepts to remove material. That is, a structuring of a second cavity $58_2$ may be performed into the silicon wafer 62.

Figure 4I:
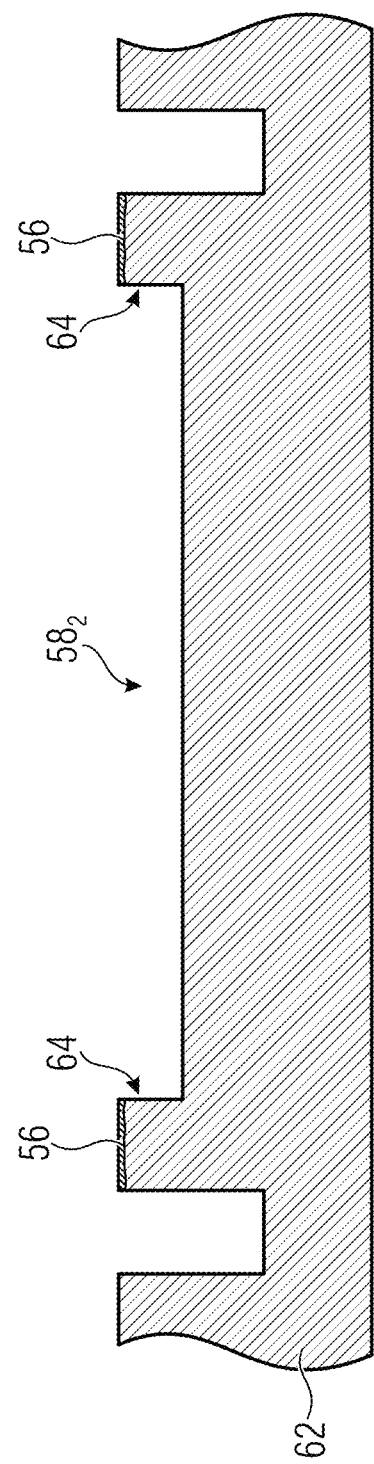
Figure 4J:
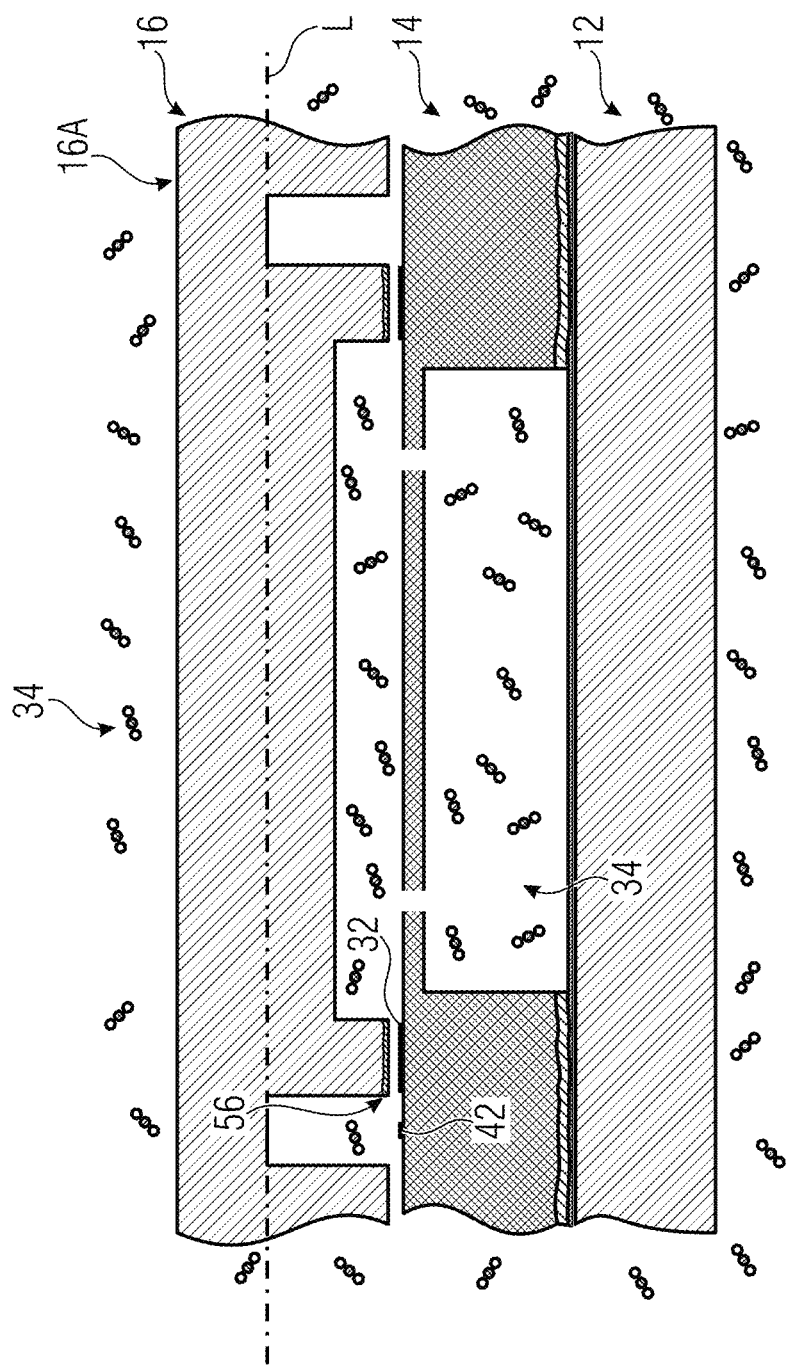

As shown in FIG. 4i, the interface forming material 56 may be arranged at contact positions or contact regions 64 of the wafer 62. That is, in regions where layer structures 14 and 16 are deemed to contact each other, the interface forming material 56 may be arranged at least partially. Alternatively or in addition, the interface forming material 56 may also be arranged at the layer structure 14. In other words, a deposition of AuSn is performed at contact position. Optionally, the coating layer $26_2$ may be arranged in recess $58_2$ prior or afterwards or simultaneously.

The structure illustrated in FIG. 4e and the structure illustrated in FIG. 4i may both be arranged into a processing chamber that may comprise the target medium 34. It is to be noted that the wafer level bonding being described in connection with FIG. 4e may also be performed in an atmosphere having the target medium 34. Alternatively, the wafer level bonding described in FIG. 4e may be performed under a different atmosphere when compared to the wafer level bonding of FIG. 4j. This may allow for hosting different media, pressures, or concentrations of gases in different sub-cavities being sealed from each other. One of such sealed cavities may also comprise a low pressure or vacuum, that is, the processing chamber may be evacuated when performing the wafer level bonding. Based on the coating layer 32 and the interface forming material 56 and by performing a wafer level bonding, layer structures 14 and 16 may mechanically be connected to each other. It is noted that wafer level bonding of layer structures 12 and 14 may be performed simultaneously or after having bonded layer structures 14 and 16.

In other words, a wafer bonding of the top sealing wafer 16 may be performed on a metallization of the microphone (here: AuSn—Au bond). Other bonding techniques, i.e., other materials are possible. The process may be done under a target atmosphere, e.g., $CO_2$. Depending on the target gas to be detected, also one or more different atmospheres may be chosen.

Figure 4K:
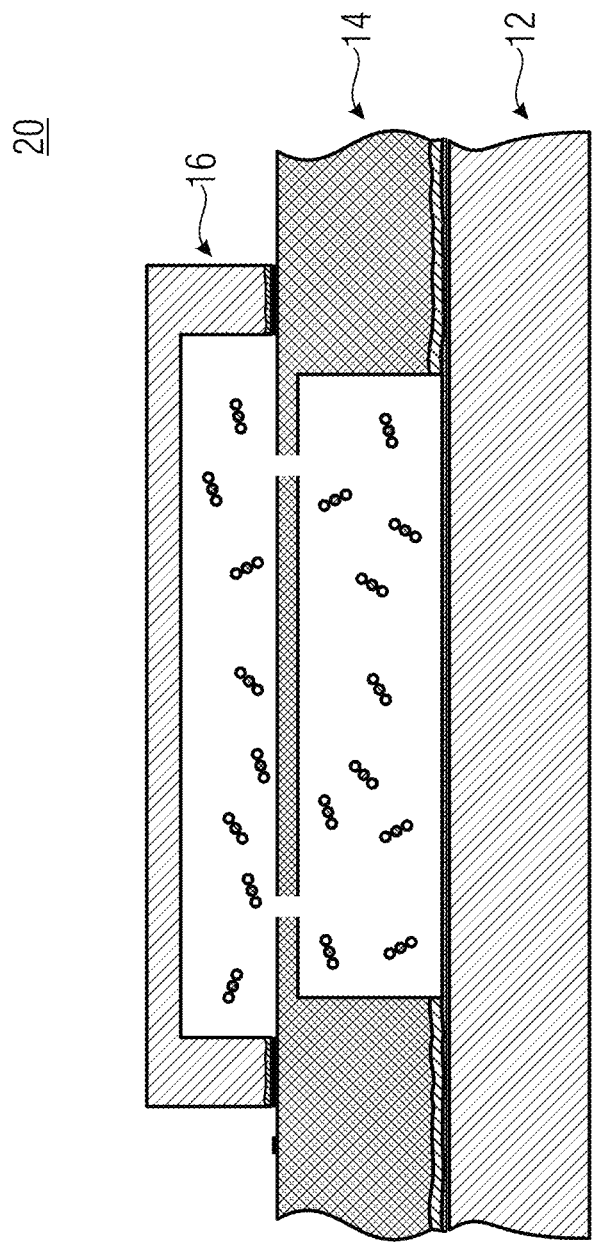

After having performed the wafer level bonding, the single detector cells may be separated from each other by removing a part of the layer structure 16, for example, starting from a side 16A, e.g., a top side, until the line L such that a configuration similar to FIG. 4k may be obtained. Layer structures 12 and/or 16 may be diced as those structures are mechanically robust.

In other words, the final device may comprise a Si-microphone with a top and a bottom sealing wafer 12 and 16. A target media ($CO_2$) is enclosed within the Si-microphone back volume as well as the cavity between the Si-cap and Si-microphone top side. The design of the Si-cap can be adjusted, e.g., the height of the cavity. Also, the overall shape of the resulting cap after singulation can be adjusted as shown, for example, in FIG. 2, e.g., with more DRIE (deep reactive ion etching processes) during structuring before the WLB process. A dual backplate Si-microphone may be used, wherein also different SiMiC (silicon microphone) technology may be used. A bottom sealing wafer, which may allow for an easy handling. However, this does not preclude a wafer having a topography from being handled. For example, the Si wafer may be coated with Au which may include a Ti adhesion layer. A HF dip may be used to remove native $SiO_2$ on a MEMS backside. An Au/Si eutectic bond may be performed, for example, using approximately 360° C. The top wafer may be processed by processing a Si cap wafer, which can be done on a carrier wafer. An AuSn/Au diffusion bond may be performed, e.g., by applying a temperature of approximately 320° C. Then, a release may be performed.

Figure 5:
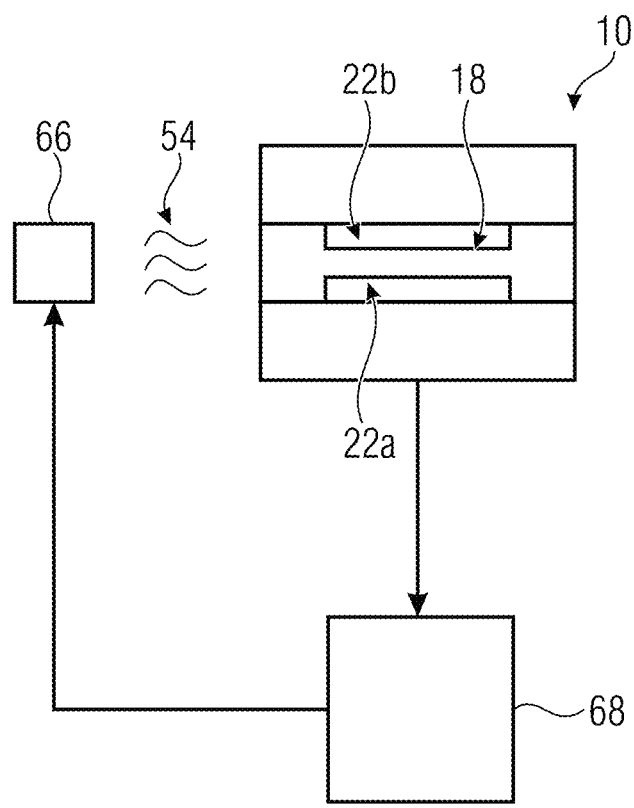
FIG. 5 is a schematic block diagram of a photoacoustic gas sensor according to an embodiment.

FIG. 5 shows a schematic block diagram of a photoacoustic gas sensor according to an embodiment. The photoacoustic gas sensor 50 may comprise the detector cell 10, wherein alternatively or in addition one or more different detector cells may be arranged, for example, detector cell 20 and/or 3o. The photoacoustic gas sensor may comprise an electromagnetic source 66 configured for emitting the electromagnetic radiation 54 so as to excite a movement of the membrane structure 18 based on an asymmetric energy absorption of the electromagnetic radiation in sub-cavities 22a and 22b of the cavity of the detector cell.

The photoacoustic gas sensor 50 may comprise a control unit 68 configured for evaluating the vibration of the membrane structure 18 and/or for controlling the electromagnetic source 66. That is, the control unit 68 may be in communication with the detector cell 10 and/the electromagnetic source 66. The control unit 68 may comprise, for example, a processor, a microcontroller, a field programmable gate array (FPGA) and/or an application specific integrated circuit (ASIC).

The detector cell 10, the detector cell 20 and/or the detector cell 30 may be obtained by processing on a wafer level. Embodiments relate to a chip-scaled packaging of a photoacoustic gas sensor, i.e., to chip-scaled packaged photoacoustic gas sensors.

Figure 6:
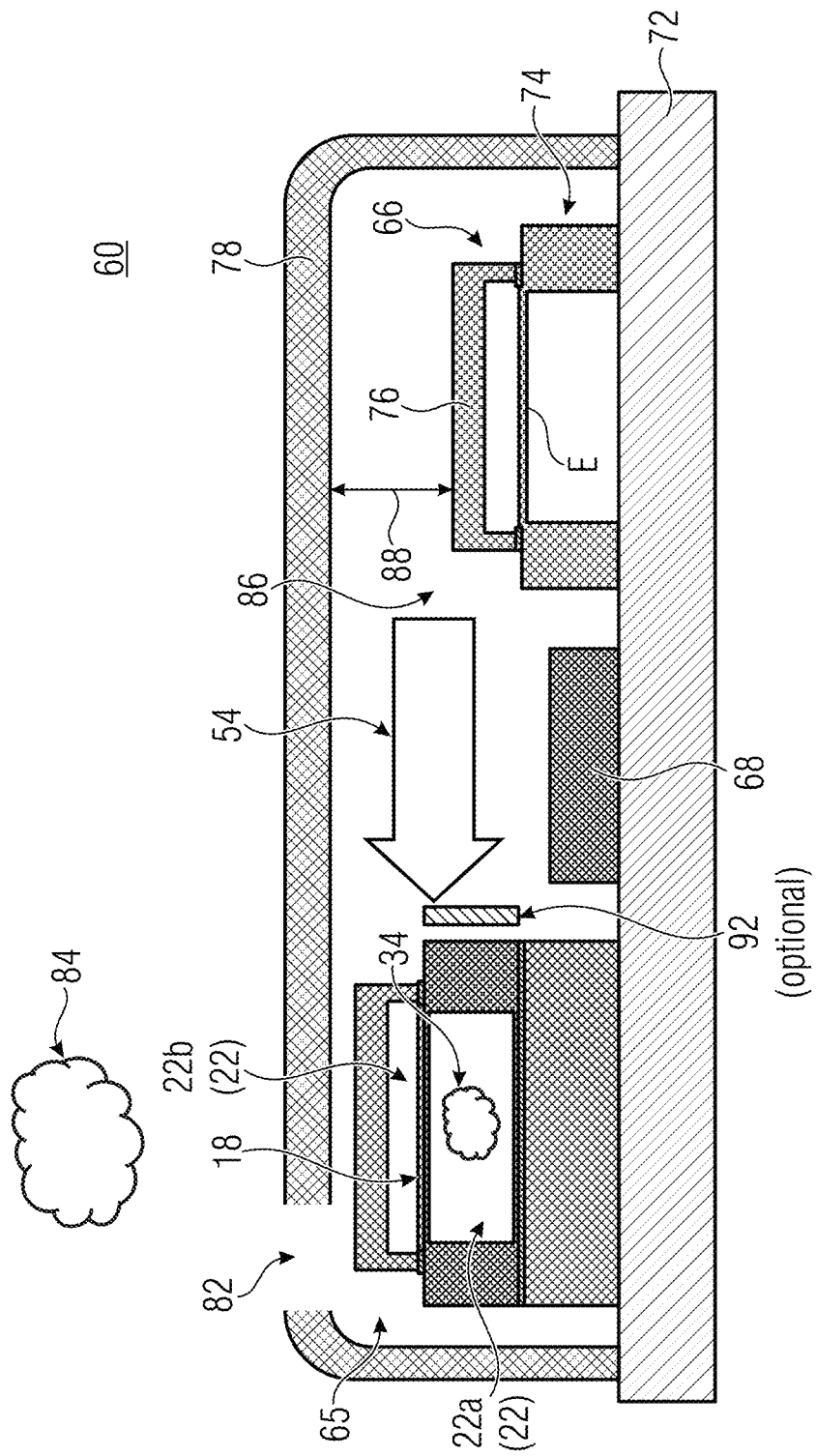
FIG. 6 is a schematic block diagram of a chip-scaled packaged photoacoustic gas sensor according to an embodiment.

FIG. 6 shows a schematic block diagram of a chip-scaled packaged photoacoustic gas sensor 60 according to an embodiment. The chip-scaled packaged photoacoustic gas sensor 60 may comprise a detector cell 65. The detector cell 65 may have a membrane structure, e.g., the membrane structure 18 inside a detector cell cavity, e.g., cavity 22. Sub-cavities 22a and 22b of cavity 22 may be arranged on different sides of the membrane structure 18. The chip-scaled packaged photoacoustic gas sensor 6o may comprise the electromagnetic source or emitter 66 which may comprise a spacing 74 and a casing 76 and an emitting element E that may generate the electromagnetic radiation 54, for example, based on a heating. That is, the element E may be a heater. Alternatively, the element E may be a black body or the like.

The electromagnetic source 66 may be configured for emitting the electromagnetic radiation 54 so as to excite a movement of the membrane structure 18 based on the described asymmetric energy absorption of the electromagnetic radiation 54 in sub-cavity 22a and sub-cavity 22b. The chip-scaled package photoacoustic gas sensor may be implemented such that the sub-cavities 22a and 22b have different sizes and/or different surface ratios so as to at least partially obtain the asymmetric energy absorption as described for the detector cells. The electromagnetic source 66 may be implemented to provide for a pulsed excitation of the electromagnetic radiation 54, e.g., based on a respective control signal. A frequency of the pulsing and/or a wavelength of the signal may be adapted to the target gas and/or the resonance frequency of the membrane structure.

The electromagnetic radiation 54 may be referred to as light even if comprising harshly or completely invisible wavelengths when compared to human abilities. For example, the detector cell 65 may be implemented as described for the detector cell 10, 20 and/or 3o. Alternatively, a configuration may be implemented in which sub-cavities 22a and 22b are sealed from each other. The target medium 34 may be arranged in at least one sub-cavity 22a and/or 22b. The possible other sub-cavity may comprise a different target medium or no target medium, i.e., it may be evacuated.

As will be described, the asymmetric energy absorption may be based on an asymmetric energy input into the sub-cavity 22a and the sub-cavity 22b from the electromagnetic radiation 54. Alternatively or in addition, the asymmetric energy absorption may be based on an asymmetric energy loss from sub-cavity 22a and sub-cavity 22b. Such an energy loss may be obtained, for example, by having different sizes of wall structures surrounding the cavities and/or different thermal conductivity. The energy loss may thus be based on an energy input of the electromagnetic energy or electromagnetic radiation into the sub-cavities 22a and 22b. The energy loss may thus be related to a thermal loss path that may lead to a reduction of resulting pressure in the target medium 34, e.g., by cooling due to the energy loss.

The chip-scaled packaged photoacoustic gas sensor 60 may comprise a substrate 72 on which the detector cell 65, the electromagnetic source 66 and/or the control unit 68 may be arranged. The substrate 72 may comprise a semiconductor material or a glass material or a ceramic material or a combination thereof. So as to allow for a low thermal loss, the electromagnetic source 66 may be spaced from the substrate 72 by a spacing structure 74 and/or encapsulated by a casing 76. The electromagnetic source 66 may form an emitter together with the casing 76. The emitter may include a filter for filtering a wavelength to be emitted towards the detector cell 65, for example, so as to avoid ambiguities in measurement results obtained by the control unit 68. For example, the fluid in the cavity, e.g., the target medium 34, may comprise a target frequency at which the fluid is resonant. The chip-scaled packaged photoacoustic gas sensor may be implemented so as to comprise a filter structure, e.g., as part of the housing 76 and/or of the spacing structure 74 or arranged between the emitting element E and the detector cell 65. The filter structure may be arranged for filtering the electromagnetic radiation 54 so as to attenuate a wavelength not corresponding to the target frequency in a larger amount, i.e. at least 20%, at least 30%, at least 50% or more, when compared to a wavelength corresponding to the target frequency. For example, the filter structure is incorporated in the casing 76 or the filter structure implements the casing 76.

The chip-scaled packaged photoacoustic gas sensor 60 may comprise a housing 78 forming an enclosure for at least the electromagnetic source 66 and the detector cell 65, wherein additional components may be arranged, for example, the control unit 68. That is, the chip-scaled package photoacoustic gas sensor 60 may comprise a lid 78 at least partially forming a cavity 86 of the chip-scaled packaged photoacoustic gas sensor. The cavity 86 may host at least the detector cell 65 and the electromagnetic source 66. The lid 78 may be reflective for the electromagnetic radiation. The enclosure may comprise a ventilation or opening 82 to allow environmental medium 84, e.g., air or a different medium, to travel into an interior 86 of the enclosure. That is, the chip-scaled packaged photoacoustic gas sensor may comprise an inlet so as to let pass a target medium, i.e., the environmental medium 84. The environmental medium 84 may thus be subjected to the electromagnetic radiation and may absorb energy therefrom at least in some specific wavelength ranges. In knowledge of a behavior of the membrane structure 18 in absence thereof, i.e., based on a calibration, a content of the environmental medium 84 may be determined. That is, at least a presence or concentration of the target medium 34 may be determined in the environmental medium 84.

In other words, a gas sensor cell including the WLB detector unit is disclosed. An infrared emitter may be packaged within the same housing next to a detector unit with corresponding ASIC for the read-out of the detector unit.

A distance 88 between the source 66 and side 78A may be small, for example, a preferably non-zero value of at most 1 mm, 500 µm or 100 µm. Such a small distance 88 may allow the electromagnetic radiation 54 to essentially arrive at the detector cell from a lateral side to excite the target medium 34. This may allow for a same or comparable energy input into the sub-cavities 22a and 22b.

Optionally, a shielding 92 may be arranged between the electromagnetic source 66 and the detector cell 65. The shielding 92 may be configured for partially shielding the detector cell 65 from the electromagnetic radiation 54 so as to at least partially obtain the asymmetric energy absorption. The shielding 92 may at least partially shield sub-cavity 22a and/or at least partially shield sub-cavity 22b. For example, only one of both sub-cavities is shielded or the sub-cavities are shielded by a different extent.

Figure 7:
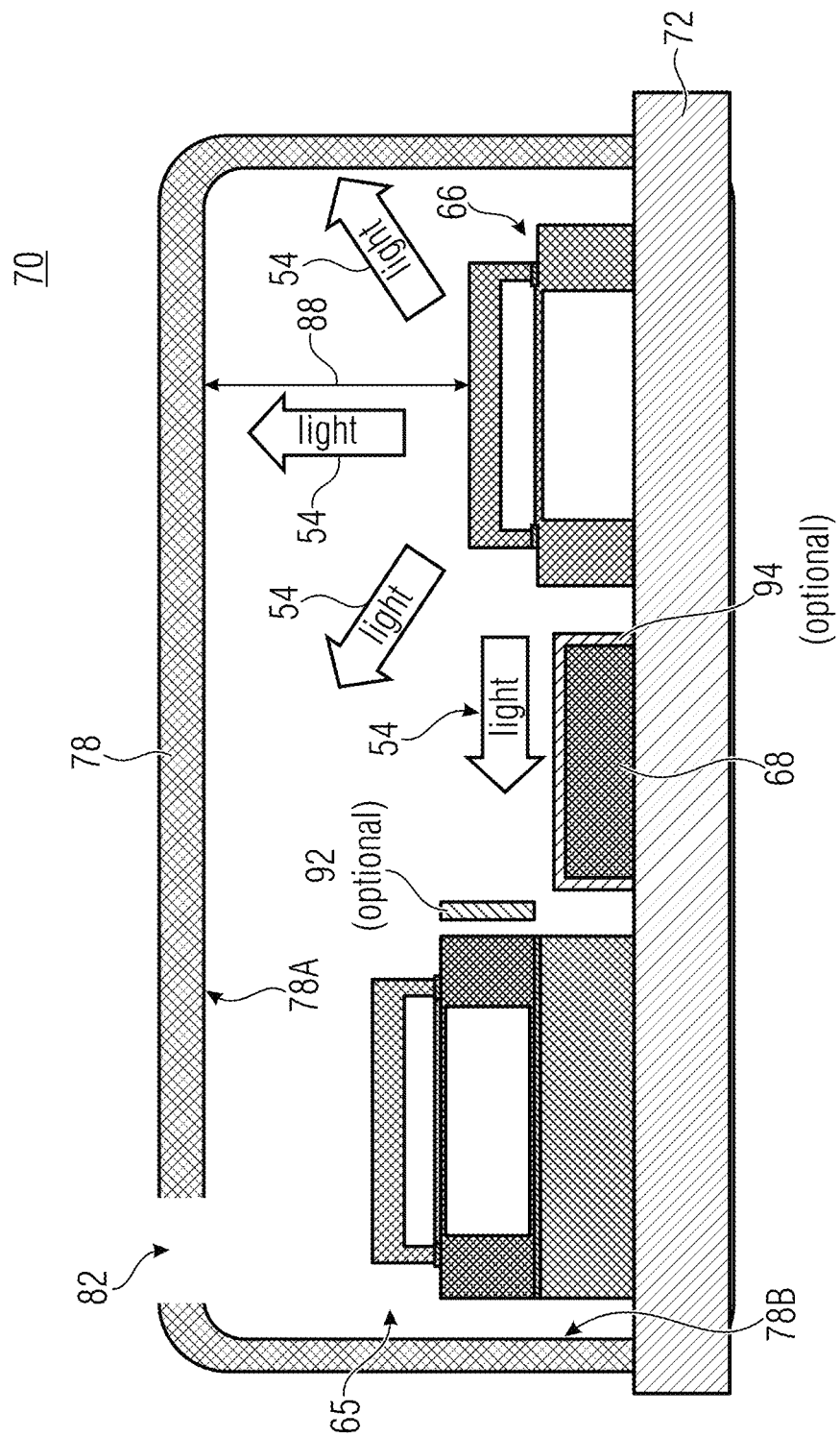
FIG. 7 is a schematic side view of a chip-scaled packaged photoacoustic gas sensor according to an embodiment.

FIG. 7 shows a schematic side view of a chip-scaled packaged photoacoustic gas sensor according to an embodiment. The distance 88 may be larger when compared to the chip-scaled packaged photoacoustic gas sensor 60, for example, having a distance larger than described in connection with FIG. 6. An example value that does not limit the described embodiments may be between 0.5 mm and 5 mm, between 0.75 mm and 3 mm or between 1 mm and 2.5 mm such as 1.6 mm. The distance 88 may be measured between a main side 78A which is spaced from the emitter and the detector cell 65 by a circumferential side 78B of the lid 78. The large distance 88 may allow scattering of the electromagnetic radiation 54 towards the detector cell 65 at the main side 78A. In contrast, the small distance shown in FIG. 6 may prevent scattering of the electromagnetic radiation 54 towards the detector cell 65 at the main side 78A such that the electromagnetic radiation 54 laterally travels towards the detector cell 65.

In other words, a gas sensor unit according to an embodiment may include the WLB detector unit. An infrared emitter may be packaged within the same housing next to the detector unit with corresponding ASIC for the read-out of the detector unit. The distance from the detector top side to the lid of the sensor unit may be big enough in order to have optical access to the top side of the detector unit. The light may be scattered and reflected within the main optical shielding (module package) making it hard to determine a main angle of incidence.

The control unit 68, i.e. the circuit, may be covered with a material 94 being intransparent for the electromagnetic radiation 54. Such an arrangement is optional. Alternatively or in addition but also optionally, the control unit or circuit 68 may be insensitive for the electromagnetic radiation 54 such that in both cases, the electromagnetic radiation 54 does not harm an operation of the control unit 68.

Figure 8:
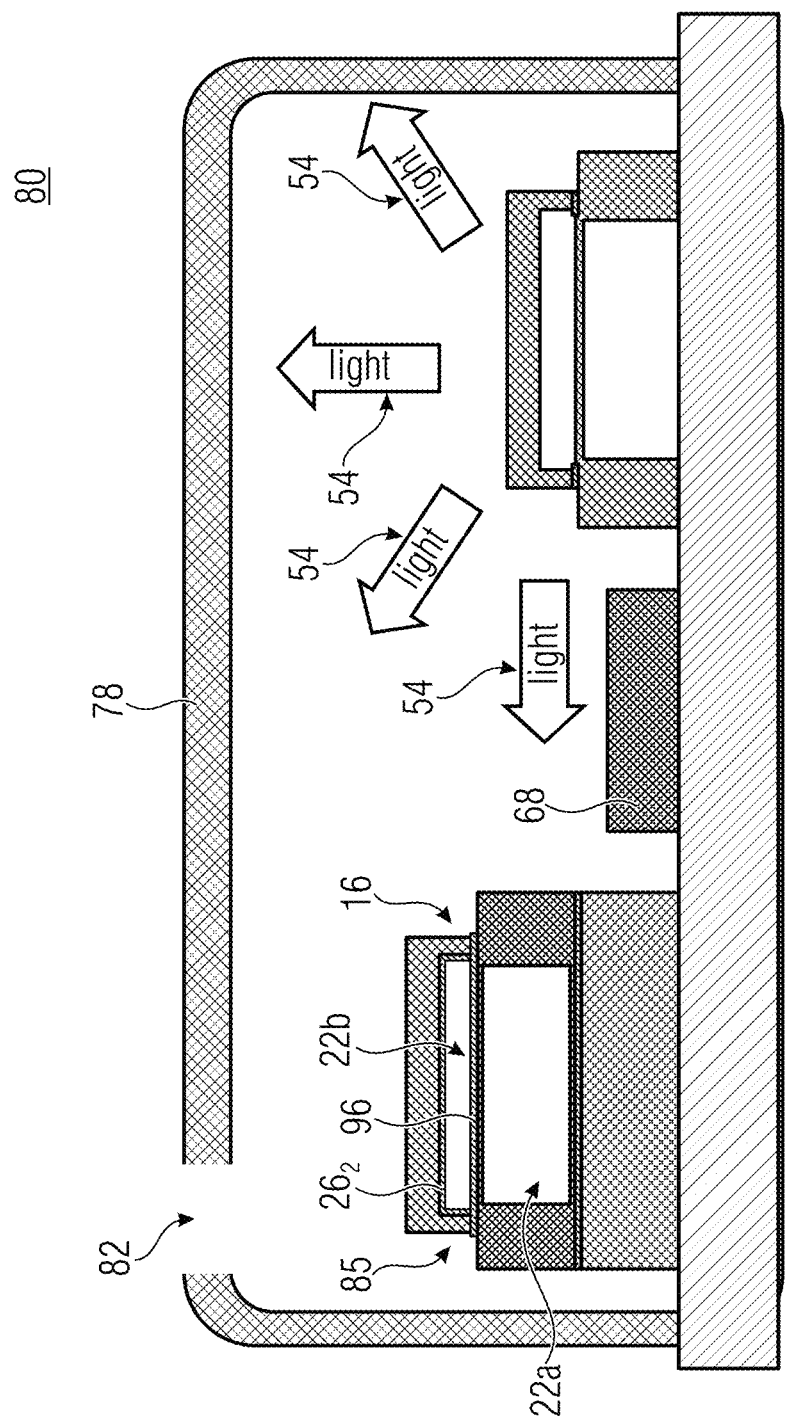
FIG. 8 is a schematic side view of a chip-scaled packaged photoacoustic gas sensor according to an embodiment, having a lid.

FIG. 8 shows a schematic side view of a chip-scaled packaged photoacoustic gas sensor 80 according to an embodiment. The lid 78 may be formed as described in connection with the chip-scaled packaged photoacoustic gas sensor 70 but may also be formed as described for the chip-scaled photoacoustic gas sensor 60. When compared to the detector cell 65, a detector cell 85 of the chip-scaled photoacoustic gas sensor 85 comprises a reflective coating $26_2$ completely or at least to an amount of more than 50%, more than 70% or more than 90% covering or shielding one of the sub-cavities 22a or 22b, e.g. sub-cavity 22b. Such a reflective coating $26_2$ may be applied, for example, to an electrode 96 of the single backplate configuration or dual-backplate configuration of the microphone chip to prevent the light from shining through the bottom interface of the top volume, i.e. to prevent the electromagnetic radiation 54 to travel through the sub-cavity 22b to the sub-cavity 22a.

In other words, the WLB may include a reflective coating of the inner or outer surfaces of the top sealing cap wafer, i.e. layer structure 16. Thus, direct optical access into the upper gas volume 22b can be avoided.

Figure 9:
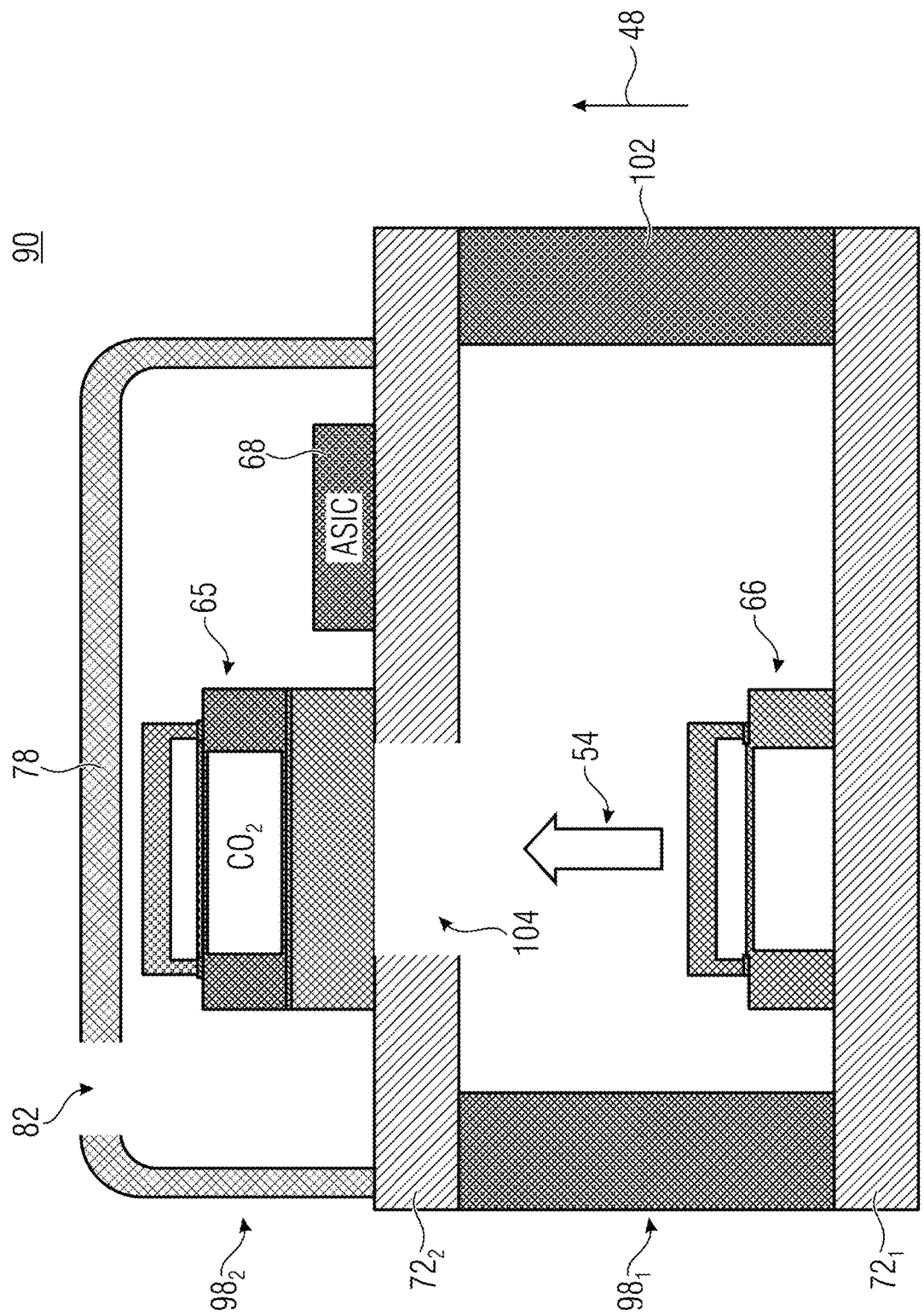
FIG. 9 is a schematic side of a chip-scaled packaged photoacoustic gas sensor according to an embodiment comprising a stacked configuration.

FIG. 9 shows a schematic side of a chip-scaled packaged photoacoustic gas sensor 90 according to an embodiment. When compared to the chip-scaled packaged photoacoustic gas sensor 60, 70 or 80, the chip-scaled packaged photoacoustic gas sensor 90 may comprise a stacked configuration. Different sub-packages $98_1$ and $98_2$ may be stacked with regard to each other and may thus extend to a different perpendicular extension when compared to the chip-scaled packaged photoacoustic gas sensors 60, 70 and 80. Whilst reducing a required surface with the stacked arrangement, a height may be increased. Sub-package $98_1$ may comprise the electromagnetic source 66, for example including a filter. Along the thickness direction 48 sub-package $98_2$ may be spaced with a spacing structure or spacer or thermally decoupling element 102 being arranged between a substrate $72_1$ and a substrate $72_2$ of the sub-packages $98_1$ and $98_2$. The thermally decoupling element 102 may comprise a low thermal conductance. For example, a polymer material or the like may be used.

Sub-package $98_2$ may comprise the detector cell 65. The control unit 68 may be arranged in sub-package $98_1$ or $98_2$. The electromagnetic radiation 54 may travel from the sub-package $98_1$ to the sub-package $98_2$. For example, substrate $72_2$ may comprise an opening 104 or an area of low thermal conductance.

In other words, embodiments relate to a closed photoacoustic gas sensing cell comprising an infrared emitter, an optical filter and a detector unit (e.g., a Si-microphone) enclosed by a housing (package). The detector unit (microphone) may be enclosed in a hermetically sealed package under a defined atmosphere of the gas of interest (e.g., a specific percentage $CO_2$, a target gas in a target concentration). The package of the detector unit may be hermetically sealed over lifetime, e.g., at least 5 years and possible ranging to 15 years. This requirement may be addressed with embodiments described herein that provide for a packaging process and corresponding structures. A wafer level bonding (WLB) processes under a desired atmosphere may decrease the packaging cost per unit since the whole packaging process may be performed on all devices still on wafer level. That is, may be prevented to fill single devices individually. WLB processes may furthermore decrease the form factor of the gas sensing detector unit in comparison to a standard packaging method and therefore enables further possibilities for integration into small-scale PCBs (printed circuit board), e.g. mobile phone applications.

A hermetically sealed gas detector unit can be formed by wafer level processes, thereby the unit may comprise a microphone wafer, a top sealing wafer acting as a cap above the membrane area as well as a bottom sealing wafer. The bottom and top sealing wafer can be equipped with reflective coating for optical shielding of the upper (above the microphone membrane) or lower (below the microphone membrane) gas volume from the outside. With this packaging, a very small enclosed gas volume can be realized, depending only or at least essentially on the thickness of the microphone wafer and the cavity in the top sealing wafer above the microphone front side. Values stated for single thicknesses do not limit the process limitations. Pulsed excitation with an infrared light source may lead to a pressure difference between above and below the microphone membrane within the enclosed gas volume and may thus lead to an acoustic signal dependent on the intensity of the infrared light.

The ASIC may be covered with light non-transparent material, e.g., globe top, or may be robust against broadband light. A gas exchange may be provided through openings in the optical shielding, depending on the optical path the ventilation can be adjusted in order to enhance the gas exchange diffusion time. With more light absorbed through the optical path outside of the detector unit (higher ambient $CO_2$ concentration), the photoacoustic pressure within the detector cell may get smaller, i.e., an inverse signal may be obtained at the ASIC. The WLB photoacoustic detector unit can be included in a photoacoustic sensor comprising, for example, a chopped MEMS infrared emitter, electromagnetic source, an optical filter for wavelength selective heating of a gas, the hermetically sealed MEMS microphone using WLB processes and a housing. The system may be operated by an internal ASIC which provides the input power of the infrared emitter as well as the acoustical read-out of the WLB detector unit.

Embodiments are based on produced hermetically sealed MEMS microphones under a dedicated gas atmosphere using wafer level bonding processes. The small hermetically enclosed gas volume may be beneficial for creating a photoacoustic pressure. It is mentioned that the ration between the two volumes (above and below the microphone membrane, the sub-cavities) may be important for the response of the detector unit to chopped infrared light. Optical shielding of one of the volumes (e.g. by metal coating of the inner part of the top volume) may enhance the detector sensitivity. In general, the height of the WLB PAS (photoacoustic sensor) detector cell may be defined or at least influenced by the thickness of the three wafers (layer structures) as well as the height of the cavity above the MEMS microphone. Thus, this may form a chip-sized solution to design a hermetically sealed WLB PAS detector cell with a height range which is possibly exclusively defined by process windows for the respective three wafers. This may allow providing small WLB PAS detector cells.

As pollution is a health effect and as health concerns due to air pollution are growing, embodiments allow to decrease the form factor as well as the production cost for a hermetically closed photoacoustic detector unit. Detector cells may be a stand-alone product but may also be included into photoacoustic gas sensors. This may provide for advantages compared to NDIR (non-dispersive infrared sensor) detectors. Embodiments relate to an infrared source that is integrated into the WLB process of the detector unit, e.g. as top or bottom wafer. The optical filter wafer may be used as top or bottom sealing wafer. That is, a process for manufacturing the electromagnetic source 66 may be similar to producing a MEMS microphone. The structure 74 and/or 76 may thus include filtering properties.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

The above described embodiments are merely illustrative for the principles of the present invention. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

What is claimed is:

1. A detector cell for a photoacoustic gas sensor comprising:
    a first layer structure;
    a second layer structure arranged at the first layer structure and comprising a membrane structure; and
    a third layer structure arranged at the second layer structure;
    wherein the first layer structure and the third layer structure hermetically enclose a cavity and wherein the membrane structure is arranged in the cavity,
    wherein a first sub-cavity of the cavity at a first side of the membrane structure and a second sub-cavity of the cavity at a second side of the membrane structure are sealed from each other and comprise different gasses or gas concentrations.

2. The detector cell according to claim 1, wherein the second layer structure forms at least a part of a side wall of the detector cell.

3. The detector cell according to claim 1, wherein the second layer structure is transparent for an electromagnetic radiation.

4. The detector cell according to claim 1, wherein the cavity is acoustically isolated.

5. The detector cell according to claim 1, wherein the first layer structure and the second layer structure are attached to each other by wafer level bonding and/or wherein the second layer structure and the third layer structure are attached to each other by wafer level bonding.

6. The detector cell according to claim 1, being asymmetric with regard to a sensitivity to electromagnetic radiation of the first sub-cavity of the cavity between the first layer structure and the second layer structure and the second sub-cavity between the second layer structure and the third layer structure.

7. The detector cell according to claim 1, wherein a surface reflective for electromagnetic radiation is arranged at a surface of the first layer structure facing the membrane structure or at a surface of the third layer structure facing the membrane structure.

8. The detector cell according to claim 7, wherein the surface reflective for electromagnetic radiation comprises at least one of a reflective material and a reflective structure.

9. The detector cell according to claim 1, wherein a first extension of the first sub-cavity between the first layer structure and the second layer structure and a second extension of the second sub-cavity between the second layer structure and the third layer structure along a direction parallel to a surface normal of a main side of the membrane structure are different.

10. The detector cell according to claim 1, having a target medium between the first and the third layer structure.

11. The detector cell according to claim 1, wherein at least one of the first layer structure, the second layer structure and the third layer structure is transparent for a mid-wavelength infrared spectrum.

12. The detector cell according to claim 1, wherein for measuring a movement of the membrane structure,
the second layer structure comprises a single backplate configuration or a dual backplate configuration for the membrane structure; or
the detector cell comprises a piezoelectric or element or a piezoresistive element.

13. The detector cell according to claim 1, wherein the membrane structure comprises at least one ventilation hole.

14. The detector cell according to claim 1, wherein a part of the cavity is sealed by a reflective coating from light adapted to excite a fluid in the cavity.

15. A photoacoustic gas sensor comprising:
a detector cell according to claim 1; and
an electromagnetic source configured for emitting an electromagnetic radiation so as to excite a movement of the membrane structure based on an asymmetric energy absorption of the electromagnetic radiation in different sub-cavities of the cavity arranged on different sides of the membrane structure.

16. A chip-scaled packaged photoacoustic gas sensor comprising:
a detector cell having a membrane structure inside a detector cell cavity, a first sub-cavity of the cavity at a first side of the membrane structure; and a second sub-cavity of the cavity at a second, opposing side of the membrane structure;
an electromagnetic source configured for emitting an electromagnetic radiation so as to excite a movement of the membrane structure based on an asymmetric energy absorption of an electromagnetic radiation in the first sub-cavity and the second sub-cavity,
wherein the detector cell comprises the detector cell of claim 1.

17. The chip-scaled packaged photoacoustic gas sensor according to claim 16, wherein the asymmetric energy absorption is based on an asymmetric energy input into the first sub-cavity and the second sub-cavity from the electromagnetic radiation; and/or based on an asymmetric energy loss from the first sub-cavity and the second sub-cavity, the energy loss being based on an energy input of the electromagnetic energy into the sub-cavities.

18. The chip-scaled packaged photoacoustic gas sensor of claim 16, comprising a shielding between the electromagnetic source and the detector cell, the shielding configured to partially shield the detector cell from the electromagnetic radiation so as to at least partially obtain the asymmetric energy absorption.

19. The chip-scaled packaged photoacoustic gas sensor of claim 16, wherein the first sub-cavity and the second sub-cavity have different sizes and/or different surface ratios so as to at least partially obtain the asymmetric energy absorption.

20. The chip-scaled packaged photoacoustic gas sensor of claim 16, having a lid at least partially forming a cavity of the chip-scaled packaged photoacoustic gas sensor, the cavity hosting at least the detector cell and the electromagnetic source, wherein the lid is reflective for the electromagnetic radiation and comprises an inlet so as to let pass a target medium.

21. The chip-scaled packaged photoacoustic gas sensor according to claim 20, wherein the lid comprises a main side being spaced from the electromagnetic source by a circumferential side of the lid, wherein a distance between the main side and the electromagnetic source is implemented so as to allow scattering of the electromagnetic radiation towards the detector cell at the main side; or wherein the distance between the main side and the electromagnetic source is implemented so as to prevent scattering of the electromagnetic radiation towards the detector cell at the main side such that the electromagnetic radiation laterally travels towards the detector cell.

22. The chip-scaled packaged photoacoustic gas sensor according to claim 16, wherein a circuit for evaluating a movement of the membrane structure is covered with a material being intransparent for the electromagnetic radiation and/or is insensitive for the electromagnetic radiation.

23. The chip-scaled packaged photoacoustic gas sensor according to claim 16, wherein the electromagnetic source forms a first sub-package of the chip-scaled packaged photoacoustic gas sensor; and wherein the detector cell forms a second sub-package of the chip-scaled packaged photoacoustic gas sensor; wherein the chip-scaled packaged photoacoustic gas sensor comprises a thermally decoupling element between a substrate of the first sub-package and a substrate of the second sub-package.

24. The chip-scaled packaged photoacoustic gas sensor according to claim 16, wherein a fluid in the cavity comprises a target frequency at which the fluid is resonant, wherein the chip-scaled packaged photoacoustic gas sensor comprises a filter structure between the electromagnetic source and the detector cell configured for filtering the electromagnetic radiation so as to attenuate a wavelength not corresponding to the target frequency in a larger amount when compared to a wavelength corresponding to the target frequency.

25. A method for manufacturing a detector cell, the method comprising:
providing a first layer structure;
attaching a second layer structure having a membrane structure at the first layer structure; and
attaching a third layer structure at the second layer structure;
such that the first layer structure and the third layer structure hermetically enclose a cavity and such that the membrane structure is arranged in the cavity,
wherein a first sub-cavity of the cavity at a first side of the membrane structure and a second sub-cavity of the cavity at a second side of the membrane structure are sealed from each other and comprise different gasses or gas concentrations.

26. The method according to claim 25, wherein attaching the second layer structure at the first layer structure and/or attaching the third layer structure at the second layer structure comprises a wafer level bonding.

* * * * *